United States Patent [19]

Iriguchi et al.

[11] 4,059,107
[45] Nov. 22, 1977

[54] TWO STEP TYPE PRESSURIZED INJECTOR

[75] Inventors: Norio Iriguchi, Oak Park, Israel; Toru Kuroda; Naoya Kominami; Kenji Inagaki, all of Fuji, Japan

[73] Assignee: Asahi Kasei Kogyo Kabushiki Kaisha, Osaka, Japan

[21] Appl. No.: 684,314

[22] Filed: May 7, 1976

[30] Foreign Application Priority Data

May 8, 1975 Japan .................................. 50-54226

[51] Int. Cl.² ............................................. A61M 5/30
[52] U.S. Cl. ................................. 128/173 H; 222/380
[58] Field of Search ............ 128/173 H, 215 R, 218 R, 128/218 F, 213; 91/443, 449, 35; 184/105 A; 222/380

[56] References Cited

U.S. PATENT DOCUMENTS

| 2,921,582 | 1/1960 | Sadd | 128/173 H |
| 3,768,472 | 10/1973 | Hodosh et al. | 128/173 H |
| 3,805,783 | 4/1974 | Ismach | 128/173 H |

FOREIGN PATENT DOCUMENTS 959,397  6/1964  United Kingdom ............ 128/173 H

Primary Examiner—Robert W. Michell
Assistant Examiner—Henry J. Recla
Attorney, Agent, or Firm—Armstrong, Nikaido & Marmelstein

[57] ABSTRACT

A two step type pressurized injector comprising as main parts, a medicine chamber for holding an injecting liquid, a piston for pressurizing the injecting liquid, a nozzle hole for ejecting the injecting liquid, a power means for displacing said piston and a regulating means for regulating the displacement of said piston is provided. This injector gives less irritation i.e. pain to the skin of a person who is receiving the injection and less external injury to the skin. The injection is carried out under a pressure of 120 Kg/cm² or higher to effect rapid perforation to a skin and then under a pressure of 100 Kg/cm² or lower after the perforation.

7 Claims, 6 Drawing Figures

TWO STEP TYPE PRESSURIZED INJECTOR

DESCRIPTION OF THE INVENTION

This invention relates to an injector or syringe for medical treatment. This invention relates particularily to a pressurized injector. The pressurized injector herein referred to is an injector in which an injecting liquid is ejected from a nozzle at a high speed and under a high pressure. It is known as an injector which enables us to effect sterile infusion or injection of vaccine or other medicine by pressing the hole of a nozzle to the skin of a person who is going to be injected, without using a needle of syringe. The infusion or injection to the skin referred to herein includes any of subcutaneous injection, intramuscular injection and intracutaneous injection.

Conventional pressurized injectors have a medicine chamber for holding an injecting liquid, a piston for pressurizing an injecting liquid and a nozzle hole for ejecting an injecting liquid. It has an advantage in that it enables us to effect injection within much shorter time than in case of a syringe provided with a syringe cylinder and a needle but it has also a drawback in that it is accompanied with irritation i.e. pain to skin at the time of infusion.

We have been continuing our strenuous works to attain an object of providing as a pressurized injector, those which enable us to effect injection with accompaniment of much less pain than conventional pressurized injectors. As the result of such works, we have found that pressurized injection can be effected almost without accompaniment of pain by finishing a perforation of a skin with an injecting liquid under a high pressure of 120 $Kg/cm^2$ or higher, within a short time of 0.05 second or less and continuing the intracutaneous injection under a lower pressure of 100 $Kg/cm^2$ or lower, and completed the present invention.

By using a two step type pressurized injector according to the present invention, it is possible to effect injection by regulating the pressure of an injecting liquid in two steps. Namely, it is possible to eject an injecting liquid at first, under a high pressure of 120 $Kg/cm^2$ or higher and thus to effect a perforation of skin of a person who is going to be injected, within a short time. Once a perforation of skin is effected, it is possible to inject the liquid under a low pressure of 100 $Kg/cm^2$ or lower. As the result, it has become possible to effect injection which gives less irritation i.e. pain to the skin of a person who is going to be injected and less external injury to the skin.

The present invention resides in a two step type pressurized injector comprising a medicine chamber for holding an injecting liquid, a piston for pressurizing an injecting liquid, a nozzle hole for ejecting an injecting liquid, a power means for displacing said piston and a means for regulating the displacement of said piston.

In the injector of the present invention, the hole diameter of a nozzle for ejecting an injecting liquid is in the range of 0.05 - 0.5 m/m, preferably 0.1 - 0.2 m/m and the front end surface of the nozzle is nearly perpendicular to the ejection stream line of a injecting liquid. The surface which is nearly perpendicular to the injection stream line includes not only a simple plane but also curved surfaces. Preferably, the medicine chamber for holding an injecting liquid has a volume of 1 cc or less.

In order to effect rapid perforation to a skin, it is necessary to use an ejection pressure of 120 $Kg/cm^2$ or higher, preferably of 200 - 300 $Kg/cm^2$. The use of a pressure higher than the above-mentioned is not economical because the structure of an injector must be of a particular pressure-resistance. The time necessary for perforating a hole in a skin under a pressure of 120 $Kg/cm^2$ or higher is from 0.005 to 0.05 second, usually about 0.01 second though it depends upon the nature of skin. After a hole is once perforated, the injection of an injecting liquid in the inside of a skin under a pressure of 120 $Kg/cm^2$ or higher, often is accompanied with break of tissue and pain. After a hole is once perforated, i.e. after 0.005 - 0.05 second, it is necessary to inject an injecting liquid into the inside of skin under a lower pressure of 100 $Kg/cm^2$ or lower, preferably a pressure of 40 - 80 $Kg/cm^2$. By such a procedure, the accompaniment of break of tissue is less at the time of injection and the accompaniment of pain hardly occurs. The use of a pressure lower than the above-mentioned makes the rapid injection difficult.

The injector of the present invention will be more fully described by referring to the accompanying drawings in which.

Figure 1:
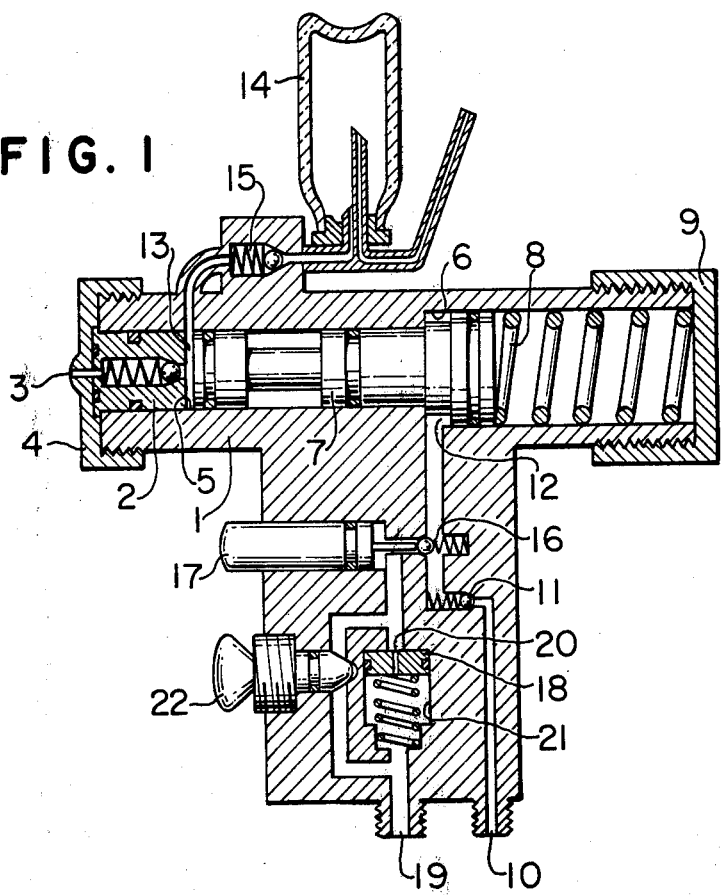
FIG. 1 shows a cross-sectional view of the principal parts of one embodiment of the injector of the present invention.

FIG. 1 shows a cross-sectional view of the principal parts of one embodiment of the injector of the present invention. Onto the front end part of the outer cylinder 1 of the injector, there is attached a cap 4 having a check valve 2 and a nozzle hole 3. The inside of the outer cylinder 1 forms a cylinder 5 for a medicine liquid in the front part thereof and a hydraulic cylinder 6 in the back part thereof. Further, inside the cylinder, there is accommodated a piston 7 in the front part and a power spring 8 in the back part. The power spring is in the state placed and compressed between the piston 7 and a cap 9 by threading said cap onto the back part of the outer cylinder 1 of the injector. When a high pressure oil (generally a non-compressible fluid is employed) is sent from an oil inlet 10, through a check valve 11 to an oil chamber 12, the oil pressure acts to move the piston backward and shorten the power spring 8 by compression. Together with the displacement of the piston 7, an injecting liquid is sent from a vial 14, through a check valve 15, to a medicine chamber 13. Once the power spring 8 has been brought to the compressed state, the oil in the oil chamber 12 is held as it is because of the presence of the check valve 11 and a check valve 16, and the power spring 8 is held in the compressed state. When a trigger 17 is pushed, the check valve 16 is opened, and since the power spring 8 presses the piston 7, the oil in the oil chamber 12 is discharged toward a piston 18 accommodated in a cylinder and having a small hole. As for the movement of oil at that time, since the piston 18 is pressed down toward an oil outlet 19, the oil is discharged in a large amount within a short time, and together with this motion, the injecting liquid in the medicine chamber 13 is compressed up to a high pressure and ejected from a nozzle hole 3 after passed through the check valve 2. After the piston 18 is forced down to the end, the oil in the oil chamber 12 is discharged only through a small hole 20 of the piston 18. Simultaneously with this discharge, the injecting liquid in the medicine chamber 13 is brought to a low pressure state and discharged from the nozzle hole 3.

Figure 2:
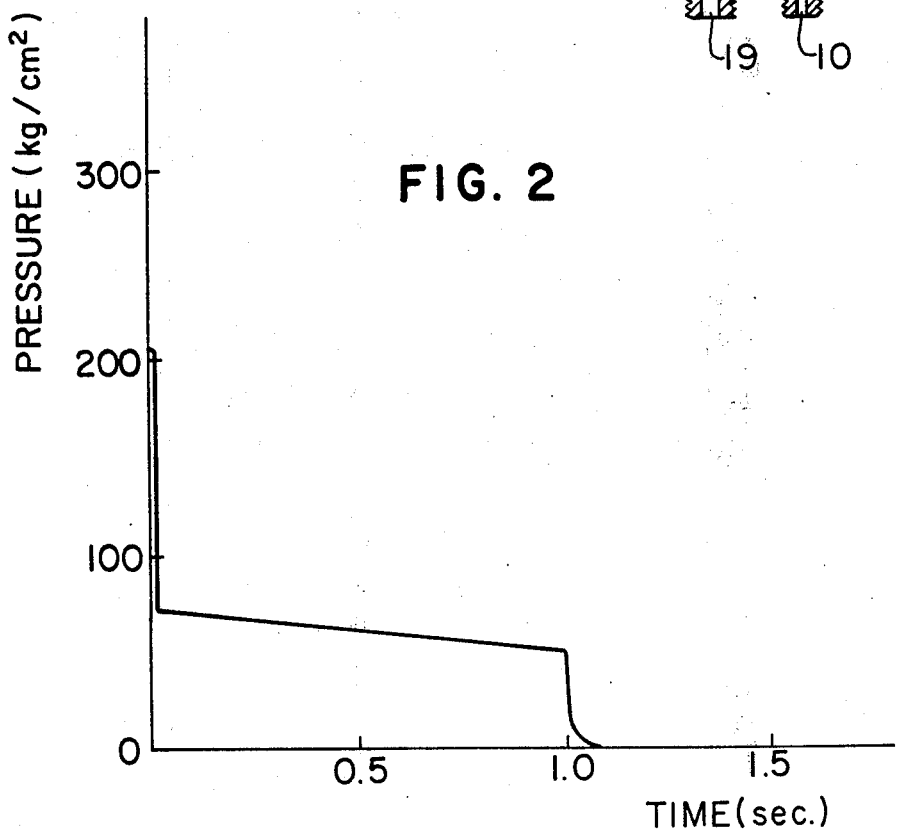
FIG. 2 shows a graph showing the change of the pressure of injecting liquid within the medicine chamber relative to time.

An example of a graph which shows the change of the pressures of injecting liquid within the medicine chamber relative to time is indicated in FIG. 2. The initial high pressure can be determined by a spring constant of the power spring 8 and a compressed distance, and it is set to a value of 120 $Kg/cm^2$ or higher, preferably a value in the range of 200 – 300 $Kg/cm^2$. The time can be easily changed by changing the volume of the cylinder 21, and it is preferably in the range of 0.005 – 0.05 second. The lower pressure can be easily changed by changing the diameter of the small hole 20, and it is set to be 100 $Kg/cm^2$ or lower, preferably in the range of 40 – 80 $Kg/cm^2$. The diameter of the nozzle 3 from which an injecting liquid is ejected is set to be in the range of 0.05 – 0.5 mm, preferably in the range of 0.1 – 0.2 mm. The front end surfaces of this nozzle is set to form a plane or curved surface approximately perpendicular to the ejection stream line. In the state where the power spring 8 is compressed by hydraulic pressure, the pressure difference between the upper stream side and the lower stream side of the piston 18 having a small hole, often brings said piston 18 to the state where the piston is fallen to the side of the oil outlet 19. In such a case, when a valve 22 is opened and thereby the pressure difference between the upper stream side and the lower stream side is removed, the piston 18 will be raised and returned to the normal position.

Figure 3:
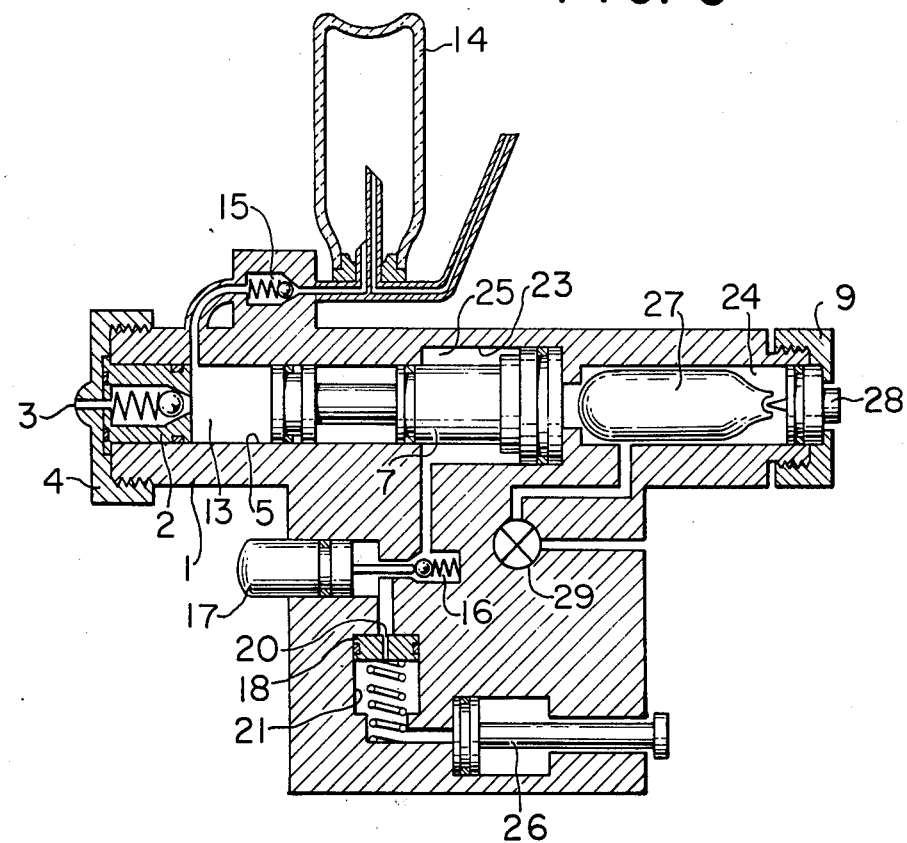
FIG. 3 shows a cross-sectional view of the principal parts of another embodiment of the injector of the present invention.

FIG. 3 is a cross-sectional view of the principal parts of another embodiment of the injector of the present invention. Onto the front end part of the outer cylinder 1 of the injector, there is attached a cap 4 having a check valve 2 and a nozzle hole 3. The inside of the outer cylinder 1 forms a cylinder 5 for a medicine liquid in the front part thereof, a fluid cylinder 23 in the middle part thereof and a compressed gas chamber 24 in the back part. Further, inside the cylinder 1, there is accommodated a piston 7 in the front part, and the fluid passage way from a fluid chamber 25, through a check valve 16 to the front end of the piston 26 is fully filled with a regulating fluid. In the state shown in FIG. 3, a chamber 13 for a medicine is filled with an injecting liquid. Then a bomb 27 in which a high pressure gas is sealed is placed in a compressed gas chamber 24. By fitting a cap 9 and a bomb cutter 28, onto the back side of the outer cylinder 1 of the injector, the sealing of the compressed-gas chamber 24 and the taking-out of the high pressure gas in the bomb 27 to the inside of the compressed-gas chamber 24 become possible. When the high pressure gas is taken out, the inside pressure of the compressed gas chamber 24 is elevated, but since a force is exerted in the direction in which the check valve 16 is closed, the piston 7 is not displaced. When a trigger 17 is pushed, the check valve 16 is opened, the pressure of the compressed-gas chamber pushes the piston 7 and the regulating liquid in the fluid chamber 25 is discharged toward a piston 18 having a small hole. At this time, as for the movement of the regulating fluid, the fluid pushes down at first the piston 18 toward the direction of piston 26 and in turn the piston 26 backward. On this account, the regulating fluid is discharged in a large amount within a short time. Following this discharge, the injecting liquid in the chamber 13 for a medicine is compressed up to a higher pressure and ejected through the check valve 2 from the nozzle hole 3. After the piston 18 having a small hole has been pushed downward, the regulating fluid in the fluid chamber 25 is discharged only through the small hole 20 of the piston, and consequently the injecting liquid in the chamber 13 for a medicine is brought to a lower pressure state and discharged from the nozzle hole 3. Thus one cycle of injection is finished, and when an injection is to be carried out again, a valve 29 is opened at first to release the high pressure gas in the compressed gas chamber to the outside thereof. If the piston 26 having been displaced backward, is pushed forward, the regulating fluid is delivered through the check valve 16 to the fluid chamber 25. On this account, the piston 7 having been displaced forward, is now drawn backward. Consequently, the injecting liquid in a vial 14 is sent through a check valve 15 to the chamber 13 for a medicine. Thereafter by closing the valve 29, arrangements for injection are completed.

In place of the bomb 27 in which a high pressure gas is sealed, a gas generator provided with a gas generating agent and an ignition mechanism can be used herein for taking out a high pressure gas.

The gas generating agent means either of combustible compositions, explosives, mixtures of the foregoing materials or those obtained by further mixing an easily decomposable gas-generating composition with the foregoing materials.

The combustible compositions comprise an oxidizing agent and a reducing agent. As the oxidizing agent, a metal oxide such as copper oxide, lead oxide or the like, a metal peroxide such as barium peroxide, strontium peroxide or the like, a permanganate such as potassium permanganate or the like, a dichromate such as ammonium dichromate, potassium dichromate or the like, a chromate such as potassium chromate or the like, and a bromate such as potassium bromate or the like are useful. As the reducing agent, a metal powder such as aluminum, magnesium or the like, a reducing non-metallic powder such as sulfur or the like, a powder of organic material such as sucrose, starch, resins and an azide such as sodium azide are useful.

The explosives include low explosives (powders) and high explosives. The low explosives are selected from black powder, a powder consisting mainly of nitrate, smokeless powder, a powder consisting mainly of ester of nitric acid, and a powder consisting mainly of a perchlorate. The high explosives are selected from initiators, high explosives consisting mainly of nitrate, chlorate or perchlorate, high explosives mainly of ester of nitric acid, nitro compounds containing three or more nitro groups.

The easily decomposable gas-generating compositions include azo compounds such as salts of azodicarboxylic acid, azide compounds such as sodium azide, ammonium salts such as ammonium oxalate, ammonium nitrate, urea, urea derivatives, aminotetrazol, aminotetrazol derivatives, hydrazine, hydrazine derivatives, guanidine, guanidine derivative and the like. Preferably those which are stable at room temperature and decompose at a temperature of 300° C or lower are selected, and one or a mixture of more than one of the selected is used. This easily decomposable gas-generating composition eases gas generation when it is mixed with a combustible composition, in case where gas formed by the decomposition of said combustible composition condenses and is harmful to attain the object of the present invention, for example, in case of a combustible composition consisting of an oxidizing agent and a metal.

It is also possible to prepare an apparatus in which the above-mentioned gas generating agent is divided into two parts in a gas generator i.e. one containing an easily igniting composition and the other containing a composition which generates a large amount of gas.

On the other hand, it does not matter even when the ignition mechanism is of percussion type or electrically initiating type. In case of percussion type, priming powder and if necessary, an anvil are used as an igniting mechanism. As in case of a common detonator for guns, the anvil can be dispensed therefrom in some cases. This ignition mechanism is further connected with a percussion needle, a spring mechanism and a trigger to effect ignition. In case of electrically initiating type, a mechanism in which thin metal wires are combined together within the gas between electric lead wires or a mechanism in which an electric spark is emitted between the gap formed between electric lead wires. This ignition mechanism is further combined with a dry cell and a switch to effect ignition.

Figure 4:
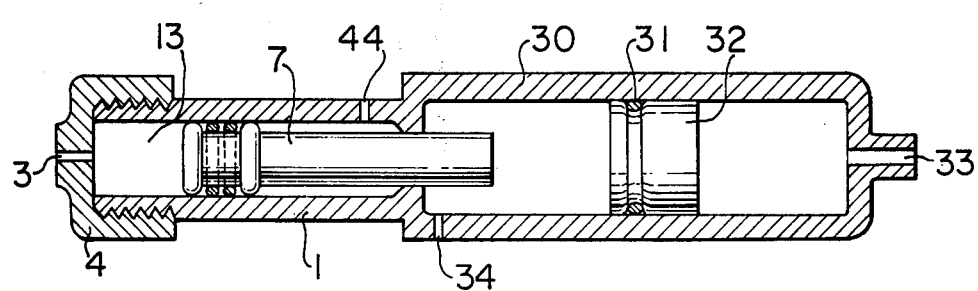
FIG. 4 shows a vertical cross-sectional view of the principal parts of a further embodiment of the injector of the present invention.

FIG. 4 is a vertical cross-sectional view of the principal parts of one embodiment of the injector of the present invention. Differently from the injector indicated in FIG. 1, there is no spring inside a backward cylinder 30. In place of it, there are installed a piston 32 having an O-ring 31, which can be freely displaced, and further gas flow ports 33 and 34.

When a high pressure combustion gas or a compressed gas is introduced from the flow port 33, the piston 32 is displaced forward within the inside of the backward cylinder 30, accelerated, endowed with dynamical momentum and brought into collision with the piston 7 whereby an impulse is imparted to the piston 7 to start it immediately with a strong force. The piston 7 is then displaced forward only by the pressure of a high pressure combustion gas or compressed gas introduced from the flow port 33 by way of the piston 32. Depending upon the pressure of gas introduced from the flow port 33 and the length of accelerated distance of the piston 32, it is easy to set the pressure of injecting liquid ejected from the nozzle 3 to vary with time as shown in FIG. 2, i.e. to set the pressure to 120 Kg/cm$^2$ or higher within 0.05 second from starting time and thereafter to 100 Kg/cm$^2$ or lower.

Figure 5:
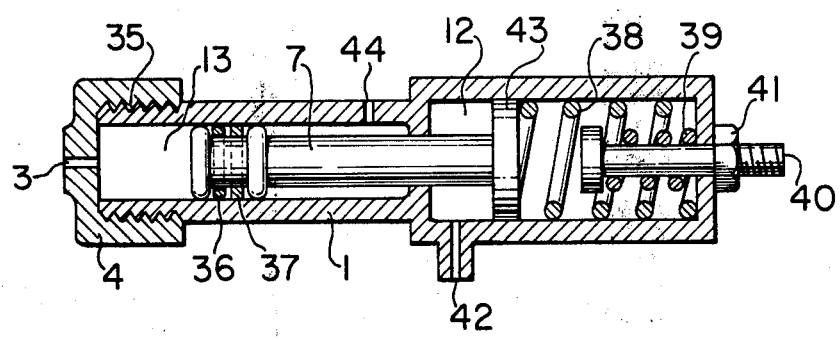
FIG. 5 shows a vertical cross-sectional view of the principal parts of the injector of the present invention in which two springs are combined.

FIG. 5 is a vertical cross-sectional view of the principal parts of an injector used to attain the object of the present invention by combining 2 springs.

A cap 4 attached to the front end part 2 of an outer cylinder 1 of injector is freely removable by a screw 35, and a desired injecting liquid can be introduced into a chamber 13 for a medicine. The piston 7 is provided with an O-ring 36 and a back up ring 37. On the back side of this piston 7, there is accommodated a spring 38 and a spring 39. The spring 39 is compressed with a bolt 40 and a nut 41, but has an allowance for compressing by other means. Numeral 42 shows a flow port for oil.

According to the structure of this injector, when a high pressure oil is introduced into an oil chamber 12 from a flow port 42 for oil, the oil acts upon the back end part 43 of the piston 7 to push it backward, compresses at first the spring 38, and pushes further the bolt 40 bacward to increase the stress upon the spring 39. When this high pressure oil is discharged to the outside by means of a valve or the like, the spring 38 as well as the spring 39 cooperate to initiate the forward movement of the piston 7 at the same time, then only the spring 38 displaces the piston 7 forward by itself to eject an injecting liquid in the chamber 13 for a medicine, from the nozzle 3 of the front end part thereof. Further in the outer cylinder 1 of the injector, there is perforated a hole 44 for withdrawing air which makes the displacement of piston 7 smoother. The injector is so arranged that the springs 38 and 39 may set the pressure exerted to the injecting liquid at the time when they at first cooperate to start the forward displacement of the piston 7, to 120 Kg/cm$^2$ or higher, and subsequently the pressure exerted to the injecting liquid at the time when the spring 38 alone moves the piston 7 forward, to 100 Kg/cm$^2$ or lower.

Figure 6:
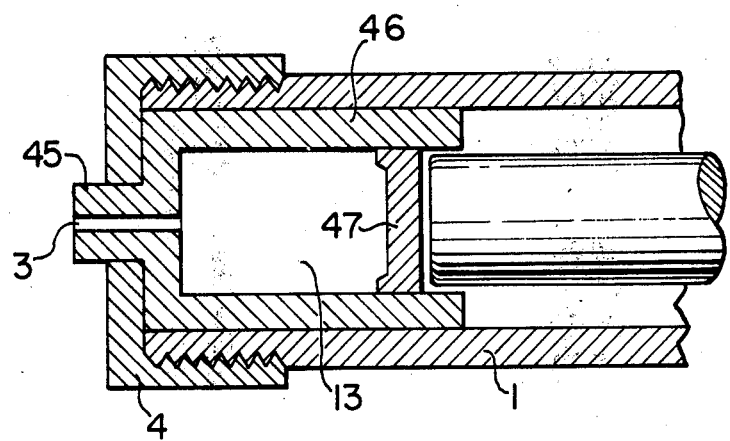
FIG. 6 shows an enlarged cross-sectional view of the ampoule part of the injector of the present invention in which an ampoule is incorporated.

FIG. 6 is an enlarged cross-sectional view of the ampoule part of one example of the injector of the present invention in which an ampoule is contained. This injector has also a two step pressure-charging means as shown in FIGS. 1, 3 and 4. An ampoule 46 containing a chamber 13 for holding an injecting liquid and having in front thereof a nozzle part 45 which has a front end surface approximately perpendicular to the ejection stream line of the injecting liquid and a nozzle hole 3 having an inner diameter of 0.05 to 0.5 mm, is fixed to an outer cylinder 1 of the injector having a perforated front end part 4 in such a way that the front end of the nozzle hole is protruded out of the above-mentioned front end part 4. A cover 47 on the back side of the ampoule 46 functions also as a piston which is displaced within the ampoule 46. Since this ampoule is disposable, there is no need of sterilization of the nozzle part and the outer cylinder of injector as in the past, and it is possible to change medicine liquids rapidly and in the sterilized state from one kind to another different kind whenever injection is to be performed. Thus it has become possible to do preparation and post-disposal for injection extremely easily and rapidly.

The ampoule 46 can be made of a relatively hard material such as aluminum, polypropylene, hard polyethylene or the like as well as of a relatively soft material such as soft fluorine resin, soft polyethylene or the like.

EXAMPLE

Using a pressurized injector having a structure as shown in FIG. 1, a pressurized injection test was carried out. A spring having a spring constant of 50 kg/cm was used as a power means. This spring was compressed by an oil under a pressure of 85 kg/cm$^2$, introduced into an oil chamber having a diameter of 22.4 mm. Next, by pushing a trigger, the oil was discharged from the oil chamber and displaced into a cylinder provided with a piston having a small hole of 0.4 mm in diameter, whereby 0.5 c.c. of a medicine liquid was totally ejected from a nozzle of 0.13 mm in diameter. The initial pressure and the second step pressure brought about by this procedure were 210 kg/cm$^2$ and 70 kg/cm$^2$, respectively. Further the time required for the ejection was 0.3 second. When a pressurized injection into a skin of person was carried out under these conditions, no pain was felt.

COMPARATIVE EXAMPLE

Using a pressurized injector having the same structure as in the injector employed in the above Example except that the cylinder for regulating the displacement of a piston by which the second step pressure is brought about, which cylinder is provided with a piston having a small hole, a pressurized injection test was carried out under the same conditions as in the above Example. The initial pressure brought about by this injector was 250 kg/cm$^2$. Further, in the case of the pressurized injection into a skin of person by means of this injector, a pain as stung by needle was felt.

What is claimed is:

1. A two step type pressurized liquid injector comprising a medicine chamber for holding an injecting liquid, a nozzle hole communicating with the medicine chamber through which the injecting liquid is ejected, a piston slidably positioned within the medicine chamber, a power means connected with the piston, the power means for operating said piston within said chamber whereby liquid therein is ejected under a pressure of at least 120 kg/cm$^2$ for a finite time up to 0.05 seconds, and a regulating means for regulating the transfer of the pressure imparted by the power means to the injecting liquid, the regulating means regulating the pressure such that the injection pressure of the injecting liquid is 100 kg/cm$^2$ or lower subsequent to said finite time and within 0.05 seconds from the initiation of the injecting of the liquid.

2. A two step type pressurized injector according to claim 1 wherein said power means comprises a means for starting said piston and exerting it upon the injecting liquid under a pressure of at least 120 Kg/cm$^2$ and a means for displacing said piston under a pressure of up to 100 kg/cm$^2$.

3. A two step type pressurized injector according to claim 3 wherein said power means is at least two springs.

4. A two step type pressurized injector according to claim 1 wherein said power means is a spring.

5. A two step type pressurized injector according to claim 1 wherein said power means is a compressed gas.

6. A two step type pressurized injector according to claim 1 wherein said power means is a gas generator.

7. A two step type pressurized injector comprising a body having a medicine chamber for holding an injecting liquid, a nozzle hole which communicates with the medicine chamber, through which the injecting liquid is ejected, a piston slidably positioned within the medicine chamber, a power means connected to the piston, the power means for operating said piston within said chamber whereby liquid therein, is ejected under a pressure of at least 120 kg/cm$^2$ for a finite time up to 0.05 seconds, a chamber for holding a non-compressible fluid, the chamber being positioned in a space between the piston and the body of the injector, and a tubular passageway, through which the non-compressible fluid is passed, connected to the chamber by a check valve, a cylinder having a piston therein connected to said tubular passageway downstream of said check valve, said piston having a small opening therein, the cylinder being a predetermined length whereby, the piston moves a predetermined distance to initially move the non-compressible fluid at a first rate, and thereafter to move the fluid more slowly through the small opening in the piston at a second rate whereby, the injection pressure of the injecting liquid is 100 kg/cm$^2$ or lower subsequent to said finite time and within 0.05 seconds from the initiation of the injecting of the liquid.

* * * * *

UNITED STATES PATENT AND TRADEMARK OFFICE
CERTIFICATE OF CORRECTION

PATENT NO. : 4,059,107
DATED : November 22, 1977
INVENTOR(S) : Norio Iriguchi et al It is certified that error appears in the above-identified patent and that said Letters Patent are hereby corrected as shown below:

In the cover page, section [75], the address of the inventor Norio Iriguchi should read ---Oak Park, Illinois--, rather than "Oak Park, Israel"

Signed and Sealed this

Thirtieth Day of January 1979

[SEAL]

Attest:

RUTH C. MASON
Attesting Officer

DONALD W. BANNER
Commissioner of Patents and Trademarks